United States Patent
Collins et al.

(10) Patent No.: US 8,547,241 B2
(45) Date of Patent: Oct. 1, 2013

(54) HUMAN WASTE BAG OVERFLOW ALARM

(75) Inventors: Timothy R. Collins, Chaska, MN (US); Brian D. Collins, Chaska, MN (US); Quentin F. Smisek, Minneapolis, MN (US); Daniel J. Smith, Lakeville, MN (US)

(73) Assignee: Medi Bag Alarm Inc., Chaska, MN (US)

( * ) Notice: Subject to any disclaimer, the term of this patent is extended or adjusted under 35 U.S.C. 154(b) by 469 days.

(21) Appl. No.: 12/969,225

(22) Filed: Dec. 15, 2010

(65) Prior Publication Data

US 2011/0140903 A1  Jun. 16, 2011

Related U.S. Application Data

(60) Provisional application No. 61/284,284, filed on Dec. 16, 2009.

(51) Int. Cl.
 *G08B 21/00* (2006.01)

(52) U.S. Cl.
 USPC .............. 340/644; 340/540; 604/17; 604/335

(58) Field of Classification Search
 USPC ................ 340/644, 500, 540, 568.6; 604/17, 604/335, 337, 338, 339, 345
 See application file for complete search history.

(56) References Cited

U.S. PATENT DOCUMENTS

| | | | | |
|---|---|---|---|---|
| 5,178,614 A | * | 1/1993 | McDowell et al. ........... | 604/332 |
| 5,375,300 A | * | 12/1994 | Chen .......................... | 24/30.5 R |
| 5,470,325 A | * | 11/1995 | Fundock ....................... | 604/332 |
| 5,617,616 A | * | 4/1997 | Cutts, Sr. ................... | 24/30.5 R |
| 6,702,794 B2 | * | 3/2004 | Blum et al. .................... | 604/335 |
| 6,764,473 B2 | * | 7/2004 | Morton ......................... | 604/334 |
| 7,066,919 B1 | | 6/2006 | Sauerland et al. | |
| 7,468,056 B2 | * | 12/2008 | Burt .............................. | 604/330 |
| 2009/0157026 A1 | | 6/2009 | Elliot | |
| 2013/0079737 A1 | * | 3/2013 | Hanuka et al. ................ | 604/318 |

OTHER PUBLICATIONS

Smart Seal Ostomy Appliance; Eden Medical, Inc.; http://www.eden-medical.com/projects/smartsealostomyapp.html.
Stomalert User Guide, copyright (c) 2010 Nikris Ltd., http://www.stomalert.co.uk.userGuide.aspx (printed Nov. 8, 2010).
Stomalert User Guide, copyright (c) 2010 Stomalert (UK) Ltd.; http://www.stomalert.co.uk/userGuide.aspx (printed Mar. 14, 2011).

* cited by examiner

*Primary Examiner* — George Bugg
*Assistant Examiner* — Edny Labbees
(74) *Attorney, Agent, or Firm* — Nawrocki, Rooney & Sivertson, P.A.

(57) ABSTRACT

An alarm unit for signaling impending overflow of a urine or ostomy (waste) bag includes an external magnet held at the end of an arm. An internal ferrous armature attracts the magnet which provides flux holding a switch element open when the magnet provides at least a predetermined flux to the switch. A clamp allows the user to fasten the unit to an edge of the waste bag with the bag walls between the magnet and the armature. When the bag contents reach the magnet, fluid force of the bag contents separates the magnet and the armature, causing the switch element to close and conduct power from a power supply to a signal element. The arm may be flexible. The switch element preferably comprises a reed switch controlling an electronic power switch.

18 Claims, 4 Drawing Sheets

HUMAN WASTE BAG OVERFLOW ALARM

BACKGROUND OF THE INVENTION

Certain medical conditions render a person incontinent. If the person is mobile, i.e., not confined to a bed or chair, he or she typically has an ostomy or urine pouching system into which feces or urine constantly flow through a tube or catheter in the person's body. Millions of people throughout the world have undergone medical procedures or have medical conditions requiring either short term or permanent use of an ostomy or urine pouch or bag. In the following disclosure, such containers will be referred to simply as body waste bags, or simply, waste bags.

Typically, such a bag is strapped or otherwise attached to the user's leg or body under their clothes. Bags are available in drainable (reusable) or disposable versions.

A person fitted with a body waste bag typically has no control over bodily fluid releases and timing and no sensation when they occur, their duration, and their volume. Thus a wearer has little idea of the remaining capacity in the bag. Once a bag fills, it will usually overflow and spill a portion of the contents. The potential for overflow of the bag is constant.

Overflow of waste bag, particularly in public, is at the least, an event fraught with embarrassment for the wearer. An overflow event may even have adverse health consequences, for example by causing infection of an existing wound or incision. But the public humiliation and embarrassment is more than sufficient for waste bag wearer to prevent overflow at all costs.

Because a waste bag is strapped under clothes to the wearer's leg or body, visual inspection requires partial disrobing. Simple tactile sensing or manipulation of the bag through one or more layers of cloth is not a reliable method to determine the remaining capacity. Alternatively, a wearer may schedule frequent time-consuming and in certain circumstances, inconvenient visual inspections. As a practical matter, the only way a patient can visually monitor the level in a bag is to disrobe sufficiently to allow inspection.

Because of these considerations, error-free visual monitoring of remaining pouch capacity in a public setting is almost impossible to achieve. The effect of this situation often causes wearers of waste bags to limit human interaction, with obvious psychological consequences.

Existing level sensing devices all have one or more disadvantages. For example, a device that mounts permanently on a disposable bag will be discarded with the bag, adding cost to the bag. Such level-sensing devices cannot be easily reset to alarm at different levels of remaining capacity. This may be important depending on the wearer's expected activities of eating, drinking, event-attending, etc.

One existing level-sensing system mounts permanently on the bag and uses a magnet and armature arrangement to sense when the bag contents reach a preselected level. This may operate successfully, but changing the time from alarming to actual overflow is not easy.

Mechanical systems may create the potential for leakage. A mechanical system may also jam or bind, creating difficulty in sensing a full bag and consequent failure to provide appropriate notice to the wearer. For example, a float within the bag may not be easy to tactilely detect through one or more layers of cloth. If an alarm function is incorporated in a float-based detector, an issue arises as to how the float level detection occurs and how the float level signal is interpreted.

Other waste bag level-sensing units are not compatible with or easily retrofitted to waste bags currently available. Such units may well require bag redesign to accommodate level sensing, making existing bag inventories and manufacturing processes obsolete.

BRIEF DESCRIPTION OF THE INVENTION

The invention to be described solves many of these problems with existing waste bag contents alarm units. The invention comprises an alarm unit including a housing having an interior space containing sensing and signaling components of the alarm unit. The housing includes a top wall with a sensing area thereon on an exterior surface of the top wall.

An arm forming part of the sensing apparatus has first and second ends. This arm is attached to the housing's top wall at the second end in a position allowing juxtaposition of the first arm end with the sensing area.

A magnet is attached to the arm's first end. The orientation of the magnet on the arm and the arm on the top wall allows juxtaposition of the magnet to the sensing area.

A switching element within the housing is mounted in juxtaposed relation to the sensing area. The switching element has open and closed states, and takes the open state responsive to juxtaposition of the magnet to the activation area, and the closed state otherwise.

A bag edge connection element adjacent to the second end of the arm is mounted on the housing's top wall. Typical bags have an edge seam formed by the union of two walls of the bag. The connection element design allows the user to attach the unit to the edge seam of the bag at either the top or side of the bag, with the magnet lying on one wall of the bag and the sensing area on the other wall. In one embodiment, the arm is attached to the top wall through the connection element.

The magnet is sufficiently close to the sensing area to hold the switch in the open state when the two bag walls between the magnet and the top wall touch each other internally. When the walls separate as the bag fills to the position of the magnet, the magnet can no longer hold the switch in the open state, and the switch then enters the closed state.

A signal element provides a humanly detectable signal responsive to the switch's closed state. The signal may be for example, an audible alarm, a vibration, or both. By "signal element" here is meant any kind of device that provides a signal detectable by the user. The signal element is electrically connected to the switching element to control flow of electrical power to the signal element.

The unit preferably includes a power supply such as a battery and an electrically activated signal element providing the humanly detectable signal responsive to power supplied by the power supply. The switch is of the type electrically connecting the power supply to the signal element when entering the closed state.

DESCRIPTION OF THE PREFERRED EMBODIMENTS

Figure 1:
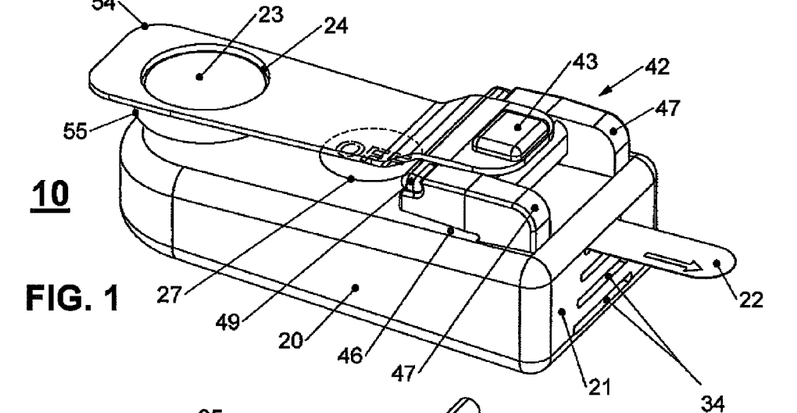
FIG. 1 is a perspective view of a waste bag contents alarm unit as typically provided to a user.
Figure 4:
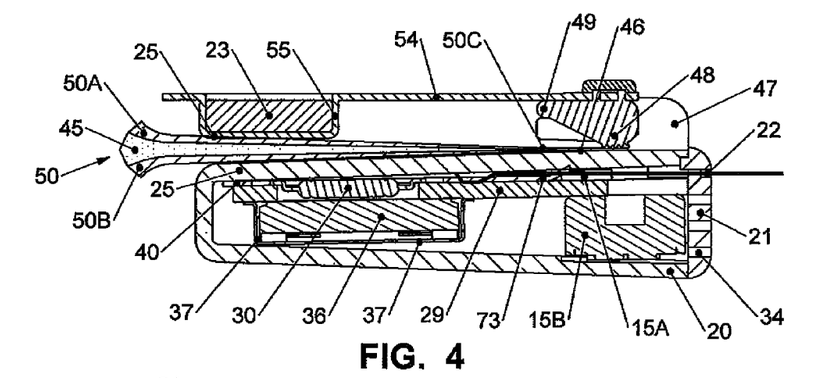
FIG. 4 is a side elevation section view of the waste bag contents alarm unit showing the arrangement of internal components.
Figure 6A:
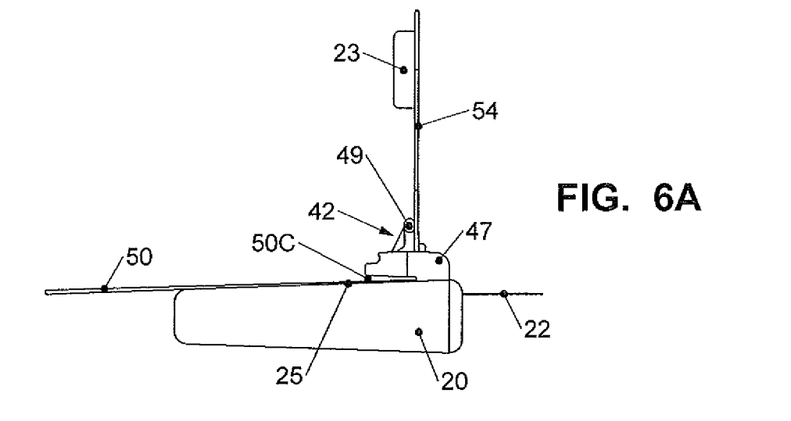
FIGS. 6A, 6B, 6C, and 6D are side elevation views of the waste bag contents alarm unit with a magnet arm in respectively, a loading position, an alarm disabling position, a sensing position, and a signaling state.
Figure 6B:
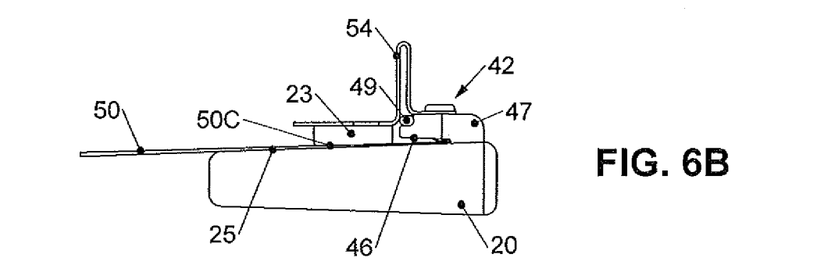

FIG. 1 is a perspective view of a sensor unit 10 for detecting impending overflow of a waste bag 50. FIGS. 4 and 6D show such impending overflow. "Impending" in this description means that overflow will possibly happen within the next few hours if bag 50 is not emptied or replaced. As one can see, the user has substantial control of the length of time between detection of impending overflow and actual overflow.

A housing 20, typically comprising molded plastic, contains the electrical components of unit 10. FIG. 1 shows a unit 10 as typically received by a customer. Pulling insulating shipping tab 22 from unit 10 activates the electrical components within housing 20. Tab 22 is shown in dotted line form in FIG. 4 to suggest that tab 22 must be removed before placing unit 10 in service.

Figure 8:
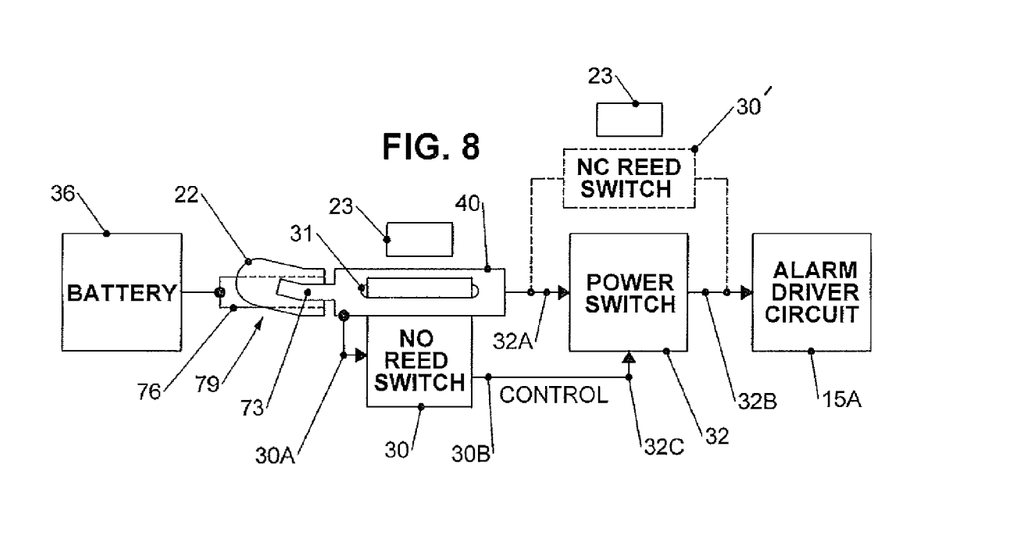
FIG. 8 shows combined electrical and mechanical diagram of the alarm circuit.

An internal circuit board 29 carries the various electrical and magnetic components of unit 10. The electrical components include a signal element 15 (see FIG. 5) for signaling impending overflow to the user, a battery 36 (FIGS. 4 and 5) serving as the power supply for unit 10, and a switching element. FIG. 8 shows the switching element as comprising either a normally closed reed switch 30', or the combination of a normally open reed switch 30 and a power switch 32.

Battery 36 may comprise a 3 v. No. CR2032 lithium button battery. While the embodiment shown for unit 10 is sealed so that battery 36 is not replaceable, in other designs, battery 36 may be rechargeable or replaceable. A battery retainer 37 holds and connects battery 36 to circuit board 29.

Figure 6C:
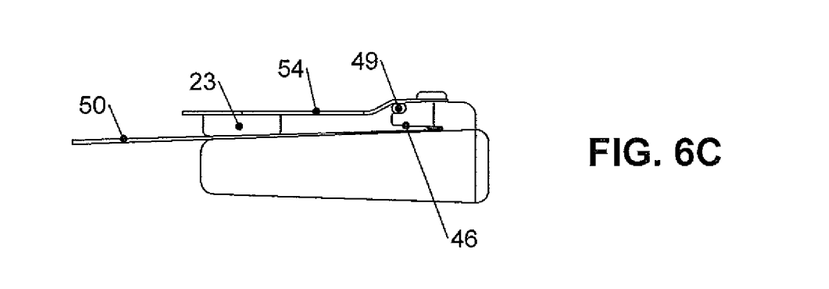
Figure 6D:
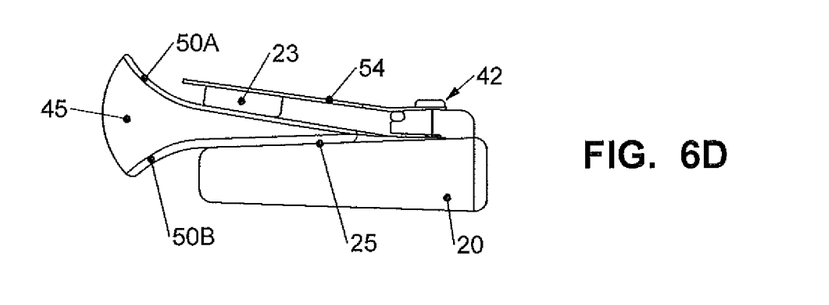

Unit 10 includes a magnet 23 which FIGS. 1, 4, and 6C show positioned on a sensing area on an upper or top wall 25 of housing 20. The "ON" legend 26 carried by wall 25 and shown in FIGS. 2 and 3 indicates the sensing area on wall 25.

Unit 10 relies on separation of magnet 23 from upper wall 25 to detect impending overflow of a waste bag 50. Waste bag 50 has an upper wall 50A and a lower wall 50B which separate (as FIG. 6D shows) when liquid or slurry within bag 50 accumulates to a point where overflow is impending. A flexible arm 54 carries magnet 23 at a first end thereof, and is mounted by an attachment means 43 at a second end to a clamping cam 48 carried by a projection 47 mounted on wall 25, thus mechanically fixing the second end of arm 54 to wall 25. In one preferred version, magnet 23 slips with a slight interference or friction fit into a well 24 near the first end of arm 54 to thereby attach magnet 23 to arm 54.

Figure 2:
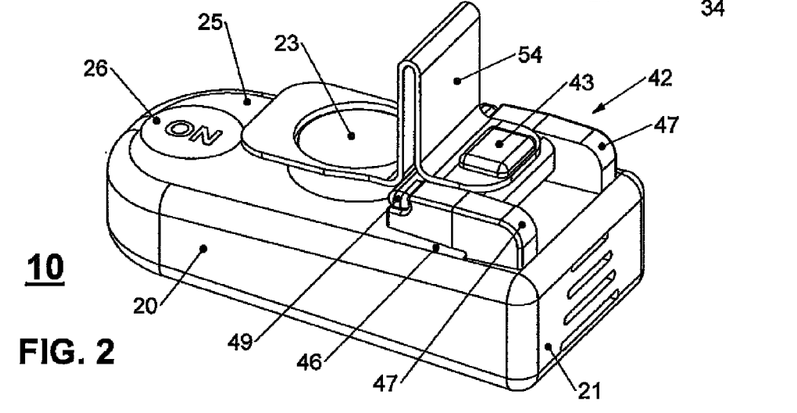
FIG. 2 is a perspective view of the waste bag contents alarm unit in disabled configuration.
Figure 3:
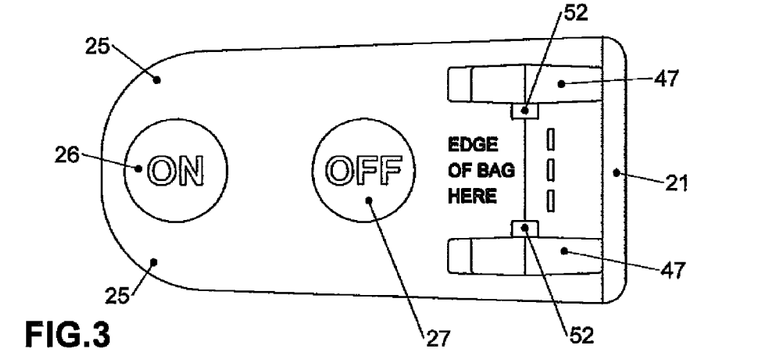
FIG. 3 is a top elevation view of the waste bag contents alarm unit with a sensing arm and clamping unit removed.

The flexibility of arm 54 allows a user, by bending arm 54 as FIGS. 2 and 6B show, to manually move or slide magnet 23 from the sensing position at ON legend 26 to an alarm disabling position indicated by an "OFF" legend 27 shown in FIGS. 1 and 3.

The user can attach unit 10 to a waste bag 50. Waste bags 50 come in a variety of designs. Typically, all have a peripheral edge 50C, often in the form of a seam, to which the user can attach unit 10 at any desired location using an integral bag clamp 42. By selecting the location on bag 50 for attaching unit 10, the user can control the amount of time or remaining bag 50 capacity between signal element 15 activation and actual overflow.

Bag clamp 42 clips unit 10 to an edge 50C of bag 50, see FIGS. 4 and 6A-6D. Although many different structures are possible for clamp 42, that shown comprises a pair of similar, side by side projections 47 shown in FIG. 10B and a clamping cam 48 (shown in FIG. 10A) having a pair of opposite-facing keyhole-like apertures 56 designed to rotate on pins 52 supported by projections 47. Projections 47 attach to wall 25 to create a pair of slots 46 between wall 25 and projections 47 into which an edge 50C of any of a wide variety of waste bag 50 designs can slide.

A lock arm 49 that is integral with cam 48 allows the user to rotate cam 48 between a loading position shown in FIG. 6A and a locking position shown in FIGS. 6B-6D. Clamping cam 48 has a series of teeth 51 facing wall 25 for positively engaging bag edge 50C. The profile of cam 48 causes the teeth 51 to approach wall 25 as lock arm 49 move toward the locking position from the loading position. In this particular design of unit 10, arm 54 mounts by attachment means 43 on a surface of cam 48 facing away from wall 25.

The spacing between cam 48 and wall 25 when arm 49 is in the loading position is such that a wide variety of bag edges 50C can enter the space between cam 48 and wall 25. The spacing between teeth 51 and wall 25 is such that when cam 48 is in the locking position, teeth 51 can securely engage edge 50C to attach unit 10 to most types of bag 50. This spacing between teeth 51 and wall 25 in the locking position may range from 0.01-0.05 in. (0.25-1.25 mm.).

Figures 5, 7, 10A, 10B:
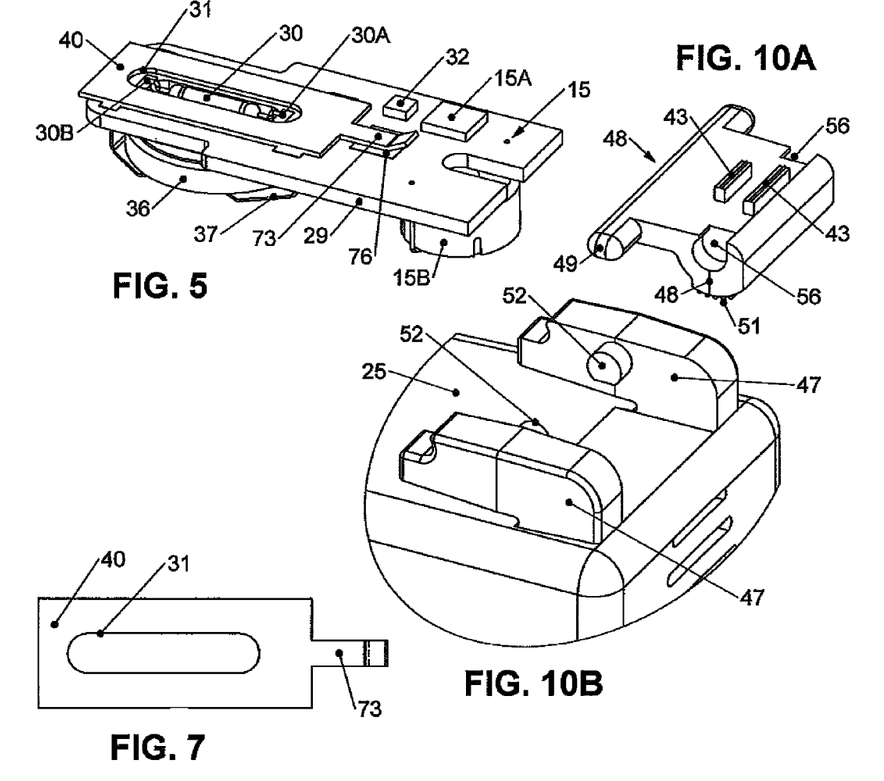
FIG. 5 is a perspective view of a circuit board and the components that it carries, for a waste bag contents alarm unit.
FIG. 7 is a top elevation view of an internal armature for conveying magnetic flux to a switch from a magnet, and forming part of the electrical connectivity on the circuit board.
FIG. 10A is a perspective view of a preferred cam forming a part of the clamping unit.
FIG. 10B is a perspective view of a detail of the unit's housing showing the structure of a preferred cam holder forming a part of the clamping unit.

FIG. 10A shows that each of the pins 52 has a flat surface facing wall 25. The flat surface on pins 52 allows cam 48 to slip onto pins 52 when in the unlocked position as shown in FIG. 6A. The maximum length of each pin 52 chord between the flat surface and the opposite curved surface is slightly greater than the opening in the respective aperture 56 to create a small amount of interference for retaining cam 48 on pins 52 when in the unlocked position.

The side elevation section view in FIG. 4 and the perspective view of the assembled circuit board 29 in FIG. 5 show the various internal electrical elements of unit 10 that circuit board 29 carries. These include a ferrous armature 40, a reed switch 30 or 30' forming a part or all of the switching element, the signal element 15, and the battery 36. Conductors (not shown) on circuit board 29 connect the electrical elements of unit 10 as the circuit diagram of FIG. 8 shows.

The circuit in FIG. 8 shows two different embodiments for the power switching element. Each embodiment employs a reed switch mounted on circuit board 29 adjacent to the sensing area and internal to housing 20. Each embodiment's reed switch has leads connecting the reed switch to circuit board 29 conductors. Both embodiments of the power switching element are within the scope of this invention.

A reed switch is a well-known type of switch whose conductive state depends on the magnetic field applied to it. Reed switches are available in both a normally open (NO) configuration, which conducts when exposed to a magnetic field having at least a predetermined flux density, and a normally closed (NC) configuration which conducts when exposed to a magnetic field less than a predetermined flux density.

Armature 40 lies on circuit board 29 within housing 20 and adjacent to wall 25, and has three purposes. First, armature 40 forms a magnetic body attracting magnet 23 to wall 25 to maintain the position of magnet 23 in the sensing and disabling positions. Secondly, armature 40 conducts flux to NO reed switch 30 or NC reed switch 30' when magnet 23 is in the alarm disabling position. Third, armature 40 forms a part of a power switch 79 closed by removing shipping tab 22.

FIG. 7 shows the shape of the armature 40. A slot or opening 31 allows armature 40 to encircle or surround reed switch 30 or 30'. Switch 30 or 30' may project a small amount into slot 31. Slot 31 provides an area on circuit board 29 within armature 40 large enough to avoid shorting switch 30 or 30' by inadvertent armature 40 contact with a switch 30 or 30' lead and at the same time conduct magnetic flux from magnet 23. Magnet 23 when in either the sensing or the alarm disabling position may be offset from switch 30 or 30' slightly as shown in FIG. 4 to more reliably hold switch 30 or 30' open.

FIG. 8 shows how armature 40 forms a portion of the electrical connection between battery 36 and signal element 15. Armature 40 is electrically connected to reed switch terminal 30A. A tab 73 of armature 40 and a contact pad 76 form the contacts of power switch 79. Pad 76 is electrically connected to battery 36. The shape and mounting of armature 40 on circuit board 29 mechanically presses tab 73 toward pad 76.

As unit 10 is shipped, insulating shipping tab 22 separates tab 73 and pad 76. The user activates unit 10 by removing shipping tab 22 to allow tab 73 to press against pad 76, closing switch 79.

A first embodiment of the power switching element shows a normally closed reed switch 30' directly controlling current flow to signal element 15. The dashed line conductors imply that NC reed switch 30' is an alternative embodiment of the power switching element. To configure the circuit of FIG. 8 as this first embodiment, NO reed switch 30 and power switch 32 must be removed from FIG. 8. Their functionality is replaced by NC reed switch 30'. Understand that in this first embodiment, NC reed switch 30' must be located within slot 31.

Positioning magnet 23 close to NC reed switch 30' as shown in FIG. 8 allows flux from magnet 23 to actuate reed switch 30' to its open circuit state. Thus, presence of magnet 23 on or near wall 25 at either of the sensing (ON legend 26) and the alarm disabling (OFF legend 27) positions holds switch 30' open.

However, a presently preferred design also shown in FIG. 8 forms a second embodiment of this invention. This second embodiment uses a normally open reed switch 30, which conducts when the ambient flux density exceeds a predetermined strength. Such a reed switch 30 controls the conductive state of an electronic power switch 32 (FIGS. 4 and 8) by providing a control signal to a control terminal 32C of power switch 32. To configure the circuit of FIG. 8 as this second embodiment, NC reed switch 30' must be removed from FIG. 8 while NO reed switch 30 and power switch 32 are present.

Power switch 32 has a terminal 32A connected to armature 40 and a terminal 32B connected to alarm driver circuit 15A. Reed switch 30 has a terminal 30A connected to armature 40 and a terminal 30B connected to the power switch 32 control terminal 32C.

Currently available reed switches of the normally open type are substantially less expensive than those of the normally closed type. Further, lithium button batteries tend to have a longer life when providing a constant current in the µampere range. These considerations make this second embodiment currently preferable.

Various types of well known power switches 32 are available that can be held the open ∥ with a control current level of a few µamperes, corresponding to a first signal level. A zero control current corresponds to a second signal level causing switch 32 to close.

FIGS. 5 and 8 together show the second embodiment of the switching circuit. When magnet 23 is physically close to switch 30 as shown in FIGS. 1, 4, 6C, and 8, magnet 23 flux holds switch 30 closed. In one preferred design, while magnet 23 is within 0.25 in. (6 mm.) of switch 30, switch 30 remains closed. When magnet 23 is near to or touching armature 40 while in the disabling position shown in FIGS. 2 and 6B, flux flowing in armature 40 also holds switch 30 closed.

The sensitivity of switch 30 and the strength of magnet 23 should be matched so that switch 30 opens when magnet 23 is approximately 0.25 in. (6 mm.) from switch 30 or from armature 40. One preferred reed switch 30 actuates to the closed state when exposed to 15-20 AT (ampere turns) of flux. (Similar considerations apply to reed switch 30' of the first embodiment.)

Magnet 23 may comprise a disc 0.125 in. (3.18 mm.) thick by 0.5 in. (12.7 mm.) in diameter, and comprising neodymium-boron alloy. The magnet 23 may have residual flux density of 14.1-14.5 KGs, coercive force and intrinsic coercive force both >11.0 KOe, and maximum energy product (BH) of 48-50 MGOe.

An armature 40 compatible with such a magnet 23 comprises a spring steel such as CRS 1012, and plated to make a good solder connection to conductors on circuit board 29. An armature 40 in a commercial embodiment is 0.016 in. (4.06 mm.) thick and 0.44 in. (11.18 mm.) wide. A thickness in the range of 0.01-0.03 in. and a width in the range of 0.375-0.625 in. appears suitable. Likely, these dimensions avoid saturation of the steel, allowing the magnet to operate switch 30 to the open state from any location on armature 40. Other types of ferrous material may also serve.

In the disclosed embodiments, wall 25 must be made of non-magnetic material. The wall 25 thickness forms a part of the magnetic circuit, so its thickness is a factor in the amount of flux that magnet 23 provides to armature 40. A commercial version of unit 10 has a wall 25 thickness of 0.07 in. (1.8 mm.).

In another possible embodiment, wall 25 itself may comprise the armature 40. In that case, a different switch 30 activation flux, strength of magnet 23, and armature/wall 40/25 will likely be required to achieve similar performance. With the guidance provided herein, a person of very ordinary skill will be able to easily select an appropriate set of component specifications.

A combination of the armature 40, switch 30, and magnet 23 shown does provide for reliably holding switch 30 closed when magnet 23 is approximately <0.30 in. (7.6 mm.) from the facing surface of armature 40. At the same time, fluidic force caused by the bag 50 level reaching unit 10 is fully able to break the magnetic attraction between magnet 23 and armature 40, reducing ambient magnetic flux to allow switch 30 to open.

The signal element 15 in unit 10 comprises in this embodiment an alarm driver circuit 15A and a speaker 15B. The element 15 design provides an audible alarm when receiving power from battery 36. A back wall 21 of housing 29 includes slots 34 that allow sound to pass easily to the user from speaker 15B.

Figure 9:
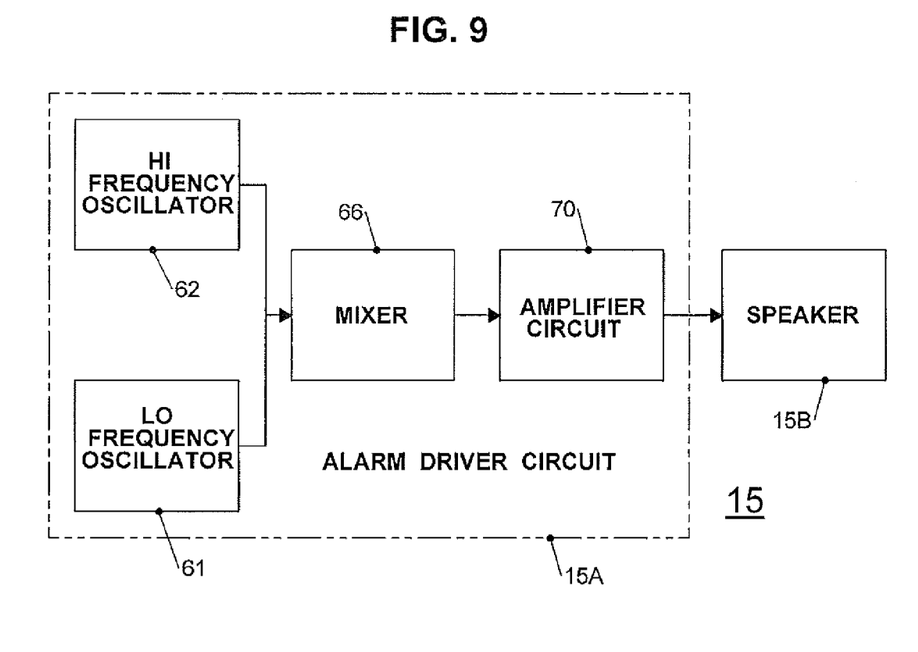
FIG. 9 shows a block diagram of the driver element in the alarm circuit.

Driver circuit 15A as shown in FIG. 9 includes low frequency oscillator 61 and high frequency oscillator 62, a mixer 66 and an amplifier 70. Speaker 15B may comprise a 4 Khz unit available from TDK as part no. PS 1240P02BT, or other suitable device.

Impending overflow as detected by opening of switch 30 provides current to driver circuit 15A. In the embodiment shown, high frequency oscillator 62 may produce an output signal to mixer 66 of from 100-5000 Hz. Low frequency oscillator 61 may produce an output signal to mixer 66 of from 2-5 Hz. A current commercial design for unit 10 uses a high frequency oscillator 62 with an output frequency of 4 KHz. and a low frequency oscillator 61 providing a 2 Hz. output.

Mixer 66 may be a FET or power transistor driven into conduction during one part of each cycle of the signal from oscillator 61, to chop the high frequency signal from oscillator 62. The mixer output is provided to an amplifier 70. Amplifier 70 provides a signal to speaker 15B to produce a sound corresponding to the mixer 66 output.

FIGS. 6A-6D include edge views of a waste bag 50. For convenience, the following discussion of FIGS. 6A-6D and other FIGS. as well will be with reference to the second embodiment of the switching element.

The proximity of magnet 23 to armature 40 at the disable alarm position as shown in each of FIGS. 2 and 6B causes flux to flow through armature 40 and to hold switch 30 closed as well. Bag 50 seams as shown in FIG. 6B are typically not thick enough to hold magnet 23 so far from armature 40 at the disabling position that magnet 23 flux is insufficient to hold switch 30 closed.

FIG. 4 shows an edge view of a waste bag 50 not yet full enough to separate magnet 23 from wall 25 sufficiently to open switch 30. In the state of FIG. 4, magnet 23 is attracted to armature 40 with flux passing through both bag walls 50A and 50B and top wall 25. In this state, magnet 23 presses on bag walls 50A and 50B adjacent to bag edge 50C. Pressure from fluid 45 is not yet sufficient to separate switch 30 and armature 40 sufficiently to allow switch 30 to close.

FIG. 6D shows a bag 50 filled to a point where the liquid 45 in the waste bag 50 has reached magnet 23. This condition allows the fluid pressure of the liquid within bag 50 to overcome the magnetic attraction between magnet 23 and armature 40 and separate magnet 23 from armature 40. The reduced flux from magnet 23 in armature 40 causes switch 30 to return to its normally open state, closing power switch 32 and allowing current flow from battery 36 to driver circuit 15A to activate speaker 15B.

The user may choose the level of fluid 45 within bag 50 where switch 30 opens to signal imminent overflow by selecting the attachment point of unit 10 to bag 50. The user will of course choose an attachment point for unit 10 to bag edge 50C that will provide adequate opportunity to empty or replace bag 50.

FIGS. 2 and 6B show magnet 23 at a disabled position, where switch 30 is held closed by flux from magnet 23 that flows through armature 40 to switch 30. Magnet 23 is resting on bag edge 50C in FIG. 6B, but this separation of magnet 23 from wall 25 in the alarm disabling position even after impending overflow is signaled, is insufficient to allow switch 30 to open.

When the unit 10 signals impending overflow, the user will often be unable to immediately empty or replace bag 50. At the same time, the user will not want unit 10 to continuously signal, as this may be distracting (in concerts for example) and in any case shorten battery 36 life. The alarm disabling position provides an option for a user to silence an alarm signal even through clothes by simply shifting magnet 23 from the sensing position of FIG. 6C to the alarm disabled position that FIG. 6B shows. The user can thus minimize disruption for the user and others near the user.

FIGS. 6A-6D show a "time progression" of how a user might use unit 10. FIG. 6A show the pre-first time use configuration, with shipping tab 22 still in place. In FIG. 6A, clamp 42 is in the loading position with lock arm 49 lifted so that bag edge 50C can be slipped between cam 48 (not visible in FIG. 6A, but seen in FIG. 4) and wall 25. A typical arm 54 has insufficient stiffness to hold magnet 23 in the position shown.

The user may attach unit 10 to either a top edge seam 50C or a side edge seam. If placed on a side edge seam, the user can select the vertical position for unit 10, to provide a selectable range of intervals between the impending overflow signal and actual overflow.

FIG. 6B shows unit 10 with the shipping tab 22 removed to activate unit 10. Lock arm 49 is in the locking position with bag 50 clamped to unit 10, and magnet 23 in the alarm disabling position with arm 54 having an approximately 180° bend. The attractive force between magnet 23 and armature 40 is sufficient to overcome any incidental shape memory restoring force that arm 54 provides. Flux from magnet 23 holds switch 30 closed. In this state of course, unit 10 will not detect impending overflow of bag 50.

FIG. 6C shows magnet 23 in the sensing position. Magnet 23 is close enough to switch 30 to hold same closed, and to armature 40 for magnetic attraction to maintain the illustrated position of magnet 23.

FIG. 6D shows unit 10 in a signaling state, with bag 50 having filled sufficiently to separate bag walls 50A and 50B and to separate magnet 23 from wall 25 and armature 40. When magnet 23 is spaced by more than about 0.3 in. (7.6 mm.) from armature 40, reed switch 30 opens, power switch 32 closes, and speaker 15B provides an audible alarm.

Once the alarm starts, the user may shift magnet 23 to the position of FIGS. 2 and 6B to disable the alarm. The user then may empty or replace bag 50 at the user's convenience, and before actual overflow occurs.

Should certain types of bags 50 not allow shifting magnet 23 to the alarm disabling position while unit 10 is still attached to a bag 50 the user still may be able to silence the alarm by pressing magnet 23 against wall 25 to overcome the fluid 45 force and again close switch 30. The user can then open clamp 42 to remove unit 10 from bag 50 while maintaining force on magnet 23. This may be important when the user is near other people in a situation where the alarm will interfere with their activity at that moment or embarrass the user.

The invention claimed is:

1. A waste bag contents unit including:
   a) a housing having an interior space, said housing including a top wall with a sensing area thereon and having a surface exterior to the interior space;
   b) an arm having first and second ends, said arm's second end mounted to the exterior of the housing's top wall at apposition allowing juxtaposition of the first arm end with the sensing area;
   c) a magnet attached to the arm's first end to allow juxtaposition of the magnet to the sensing are;
   d) a signal element providing a humanly detectable signal responsive to a switching's closed state;
   e) a bag edge connection element attached to the top wall; and
   f) within the housing, the switching element having open and closed states and connected to the signal element, and having at least a part thereof mounted in juxtaposed relation to the sensing area, said switching element taking one of the open and closed states responsive to presence at the sensing area of magnetic flux of at least a predetermined flux density, and the other of the open and closed state otherwise.

2. The alarm unit of claim 1, wherein the bag edge connection element includes a projection from the top wall and a cam mounted for rotation on the projection, said cam having a lock arm for rotating the cam, said cam having a surface approaching the top wall as the arm rotates toward a locking position.

3. The alarm unit of claim 2, wherein the cam surface includes a plurality of teeth.

4. The alarm unit of claim 3, wherein the projection defines a slot between a surface thereof facing the top wall, and the top wall, and said cam is adjacent to said slot, said slot for receiving an edge of a waste bag.

5. The alarm unit of claim 2, wherein the second arm end is attached to the cam.

6. The alarm unit of claim 1, including a power supply providing a power voltage, and wherein the signal element further comprises an electrically activated component providing the humanly detectable signal responsive to power supplied by the power supply, wherein the switching element is connected between the power supply and the signal element.

7. The alarm unit of claim 6, wherein the power supply comprises a battery and wherein the signal element comprises a sound generator.

8. The alarm unit of claim 6, wherein the switching element includes a reed switch mounted within the housing and adjacent to the sensing area.

9. The alarm unit of claim 6, wherein the switching element includes
   a) a power switch having power terminals connected between the power supply and the signal element, and having a control terminal, said power switch held open responsive to a first signal level at the control terminal, and held closed responsive to a second signal level at the control terminal; and
   b) a reed switch mounted adjacent to the sensing area and connected between the power supply and the power switch's control terminal to provide the first signal level to the control terminal responsive to ambient magnetic flux of at least the predetermined level, to open the power switch, and to provide the second signal level to the control terminal responsive to presence at the sensing area of less than the predetermined magnetic flux density, to close the power switch.

10. The alarm unit of claim 9, wherein the reed switch closes responsive to presence at the sensing area of magnetic flux of at least a predetermined strength and is open otherwise.

11. The alarm unit of claim 1, wherein the arm is flexible, and wherein the unit further comprises within the housing a ferrous armature juxtaposed to the sensing area.

12. The alarm unit of claim 11, wherein the top wall has a second end adjacent to the second arm end, and a first end adjacent to the activation area, and wherein the armature extends from the sensing area toward the top wall's second end.

13. The alarm unit of claim 12, wherein the top wall has an outside surface, and a second legend thereon spaced from the sensing area.

14. The alarm unit of claim 13, wherein the top wall has an outside surface, and a first legend thereon adjacent to the sensing area.

15. The alarm unit of claim 11, wherein the ferrous armature has an opening surrounding the switch.

16. The alarm unit of claim 11, wherein the ferrous armature is electrically connected to the switch element.

17. The alarm unit of claim 1, including a power supply providing a power voltage, and wherein the switching element comprises a reed switch connected to the power supply and controlling electrical power to the signal element.

18. The alarm unit of claim 17, wherein the reed switch is a normally closed reed switch connected between the power supply and the signal element.

* * * * *

UNITED STATES PATENT AND TRADEMARK OFFICE
CERTIFICATE OF CORRECTION

PATENT NO. : 8,547,241 B2
APPLICATION NO. : 12/969225
DATED : October 1, 2013
INVENTOR(S) : Timothy R. Collins et al.

It is certified that error appears in the above-identified patent and that said Letters Patent is hereby corrected as shown below:

In the Claims:

Column 8, Line 56, "apposition" should be --a position--.

Column 8, Line 59, "are" should be --area--.

Signed and Sealed this
Tenth Day of December, 2013

Margaret A. Focarino
*Commissioner for Patents of the United States Patent and Trademark Office*